US00PP15142P2

(12) United States Plant Patent
Olesen et al.

(10) Patent No.: US PP15,142 P2
(45) Date of Patent: Sep. 7, 2004

(54) MINIATURE ROSE VARIETY 'POULRA022'

(50) Latin Name: *Rosa hybrida*
Varietal Denomination: POULra022

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/357,673

(22) Filed: Feb. 3, 2003

(51) Int. Cl.[7] ..... A01H 5/00
(52) U.S. Cl. ..... Plt./120; Plt./116; Plt./121
(58) Field of Search ..... Plt./116, 120, 121

(56) References Cited

U.S. PATENT DOCUMENTS

PP11,242 P * 2/2000 Kordes ..... Plt./116

OTHER PUBLICATIONS

UPOV ROM GTITM Computer Database, GTI JOUVE Retrieval Software 2003/01 citation(s) for 'POULra022'.*

* cited by examiner

*Primary Examiner*—Bruce R. Campell
*Assistant Examiner*—W C Haas

(57) ABSTRACT

A new miniature rose plant which has abundant, very pale pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Botanical classification: *Rosa hybrida.*

Variety denomination: 'POULra022'.

The present invention constitutes a new and distinct variety of miniature rose plant which originated from a controlled crossing between 'Patricia Kordana', described and illustrated in U.S. Plant Pat. No. 11,242 issued on Feb. 22, 2000 and 'POULache', non-patented. The two parents were crossed and the resulting seeds were planted in a controlled environment. The new variety is named 'POULra022'.

The new rose may be distinguished from its seed parent, 'POULache', by the following combination of characteristics:

1. The seed parent has peach colored blooms, while those of 'POULra022' are nearly white.
2. The seed parent has a bloom diameter of 50 to 80 mm, while that of 'POULra022' is 35 to 40 mm.
3. The seed parent has a lower thorn incidence than that of 'POULra022'.

The new variety may be distinguished from its pollen parent, 'Paticia Kordana', created by the same inventors, by the following combination of characteristics:

1. 'Patricia Kordana' has a pink bloom color, while that of 'POULra022' is nearly white, with a faintly pink cast.
2. 'Patricia Kordana' has a petal count of 25 to 30, while that of 'POULra022' has an average petal count in excess of 50.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type, known to the inventors, distinguish 'POULra022' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra022' was selected by the inventors as a single plant from the progeny of the hybridization in 1999.

Asexual reproduction of 'POULra022' by cuttings and traditional budding was first done by L. Pernille and Mogens N. Olesen in their nursery in Fredensborg, Denmark in August of 2000. This initial and other subsequent propagations conducted in controlled environments have demonstrated that the characteristics of 'POULra022' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra022'. Specifically illustrated in the drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULra022', as observed in its growth cultivated in a glasshouse in Burlington, Canada. Observed plants are 10 weeks of age. Color references are made using The Royal Horticultural Society (London, England) Colour Chart, 1995, except where common terms of color are used.

For a comparison, several physical characteristics of the rose variety 'POULra010', a rose variety from the same inventors described and illustrated in U.S. Plant Pat. No. 13,325 and issued on Dec. 10, 2002 are compared to 'POULra022' in Chart 1.

CHART 1

| | 'POULra022' | 'POULra010' |
|---|---|---|
| Petal color: outermost petals, upper surface | Orange-White Group 159D with basal petal zone coloration of Red Group 36D | Orange Group 27 D |
| Shape of open flower when viewed from the side, upper part | Convex | Flattened convex |
| Petaloids | 50 | 2 to 3 |

Parents:

*Seed parent.*—'Patricia Kordana'.

*Pollen parent.*—'POULache'.

Classification:

*Botanical.*—*Rosa hybrida* 'POULra022'.

*Commercial.*—Miniature.

FLOWER AND FLOWER BUD

Blooming habit:

Flower bud:

*Size.*—Upon opening, 25 mm in length from base of receptacle to end of bud.

*Diameter.*—11 mm.

*Bud form.*—Globular.

*Bud color.*—As sepals unfold petals are White Group 155A to Orange-White Group 159D. At ¼ opening, petals are White Group 155A to Orange-White Group 159D.

*Sepals.*—Green Group 138A. Medium foliaceous appendages on three of the five sepals. Surfaces of sepals are moderately pubescent. Stipitate glands occur on undersides and margins. Shape: Overall shape of the sepals is subulate. Sepal apex is cirrhose. Base is flat at union with receptacle. Size: 25 to 30 mm long×8 to 10 mm wide.

*Receptacle.*—Surface: Smooth. Shape: Funnel. Size: 5 mm (h)×7 mm (w). Color: Yellow-Green Group 144A.

*Peduncle.*—Surface: Stipitates observed. No prickles observed. Length: 20 to 25 mm average length. Diameter: 2.5 mm. Color: Yellow-Green Group 144A. Strength: Upright and strong.

*Borne.*—Singly.

*Anthocyanin.*—None observed.

Flower bloom:

*Fragrance.*—Light floral scent.

*Duration.*—As a pot plant, flowers last from 8 to 10 days.

*Size.*—Average flower diameter is 35 to 40 mm when open.

*Depth.*—20 mm.

*Form.*—Shape of flower when viewed from the side: Upon opening, upper part: Convex. Upon opening, lower part: Convex. Open flower, upper part: Convex. Open flower, lower part: Concave.

*Petalage.*—Average range: 70 petals under normal conditions with 50 petaloids.

Color:

*Upon opening, petals.*—Outermost petals: Outer Side: Orange-White Group 159D at margins and middle with basal zone of Red Group 36D. Inner Side: Orange-White Group 159D at margins and middle with basal zone of Red Group 36D. Innermost petals: Outer Side: Orange-White Group 159D at margins and middle with basal zone of Red Group 36D. Inner Side: Orange-White Group 159D at margins and middle with basal zone of Red Group 36D.

*Upon opening, basal petal spots.*—Outermost petals: Outer Side: Yellow Group 1C. Inner Side: Yellow Group 1C. Innermost petals: Outer Side: Yellow Group 1C. Inner Side: Yellow Group 1C.

*After opening, petals.*—Outermost petals: Outer Side: Orange-White Group 159D at margins and middle with basal zone of Red Group 36D. Inner Side: Orange-White Group 159D at margins and middle with basal zone of Red Group 36D. Innermost petals: Outer Side: Orange-White Group 159D at margins and middle with basal zone of Red Group 36D. Inner Side: Orange-White Group 159D at margins and middle with basal zone of Red Group 36D.

*After opening, basal petal spots.*—Outermost petals: Outer Side: Yellow Group 1C. Inner Side: Yellow Group 1C. Innermost petals: Outer Side: Yellow Group 1C. Inner Side: Yellow Group 1C.

General tonality: On open flower Yellow-White Group 158D. No change in the general tonality at the end of the 8th day. Afterwards, general tonality is White Group 155C.

Petals:

*Petal reflex.*—Strongly.

*Petal edge.*—Entire with a point in the center of the margin. Some peals exhibit a notch at the center of the margin.

*Shape.*—Deltoid.

*Size.*—18 mm long×17 mm wide.

*Petaloids.*—Quantity: Commonly 40 to 50. Size: 6 mm long; 3 mm wide. Color: Yellow-White Group 158D. Shape: Elliptical.

*Thickness.*—Thin.

*Arrangement.*—Not formal.

Reproductive organs:

*Observations.*—Floral parts are incomplete.

*Pollen.*—None observed.

*Anthers.*—None observed.

*Filaments.*—None observed.

*Stigmas.*—None observed.

*Styles.*—None observed.

*Seed formation.*—Not observed.

PLANT

Plant growth: Vigorous, compact, upright to bushy. When grown as a 8–11 cm pot plant, the average height of the plant itself is 20 to 40 cm and the average width is 20 cm.

Stems:

*Size.*—15 cm length by 3.5 mm diameter.

*Internode distance.*—30 mm.

*Color.*—Young wood: Yellow-Green Group 144A. Older wood: Green Group 137A.

*Thorns.*—Incidence: 8 per 10 cm of stem. Size: Average length: 4 mm. Color: Greyed-Yellow Group 160B. Shape: Linear.

*Surface.*—Young wood: Smooth. Older wood: Smooth.

Plant foliage: Normal number of leaflets on normal leaves in middle of the stem: 5 leaflets.

*Leaf size.*—85 mm (l)×60 mm (w).

*Quantity.*—Under normal growing conditions the plants exhibit 1 leaf per 3 cm of stem.

*Color.*—Upper Leaf Surface: Green Group 137A. Lower Leaf Surface: Green Group 138B. Juvenile foliage: Upper Leaf Surface: Yellow-Green Group 144B. Lower Leaf Surface: Yellow-Green Group 144C. Anthocyanin intonation: Location: On plants grown under high light conditions, leaf margins and developing leaves may exhibit intonations of Greyed-Red Group 181A.

Plant leaves and leaflets:

*Stipules.*—Size: 7 mm (l)×4 mm (w). Color: Yellow-Green Group 144A and 144B. Presence of stipitate glands: Edges of stipules.

*Petiole.*—Length: 7 mm. Diameter: 1 mm. Color: Green Group 137A. Underneath: Yellow-Green Group 144A. Single small thorn expressed.

*Rachis.*—Size: 20 mm in length. Color: Green Group 137A. Underneath: Yellow-Green Group 144A.

*Leaflet.*—Size: 35 mm (l)×20 mm (w). Edge: Serrated. Shape: Ovate. Base is rounded. Apex is acute. Texture: Moderately glossy and thin. Arrangement: Odd pinnate. Venation: Reticulate. Yellow-Green Group 145A in color.

Disease resistance: Average resistance to mildew, black spot, and Botrytis under normal growing conditions in Burlington, Canada.

We claim:

1. A new and distinct variety of rose plant of the miniature class, substantially as herein illustrated and described as a distinct and novel rose variety due to its abundant, very pale pink flowers, vigorous growth, compact habit, suitability for production from softwood cuttings in pots, and durable flowers and foliage which make the variety suitable for distribution in the floral industry.

* * * * *

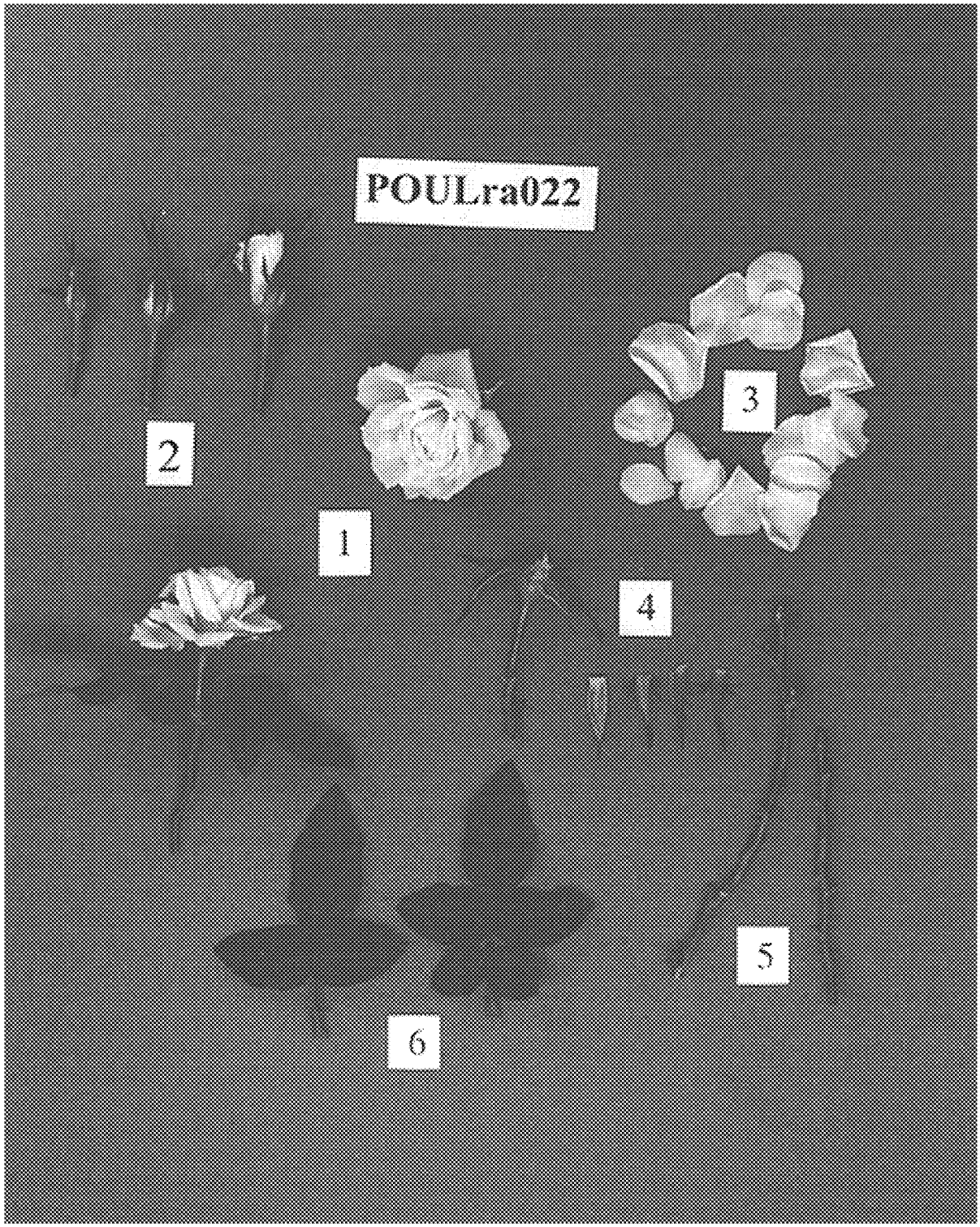
POULra022
1
2
3
4
5
6